US00PP08214P

United States Patent [19]

Orton, Jr. et al.

[11] Patent Number: Plant 8,214

[45] Date of Patent: Apr. 27, 1993

[54] DOGWOOD TREE — NAMED 'D-376-15'

[75] Inventors: Elwin R. Orton, Jr., Somerville; David A. Gant, Wall Township, Monmouth County, both of N.J.

[73] Assignee: Rutgers University, New Brunswick, N.J.

[21] Appl. No.: 740,638

[22] Filed: Aug. 5, 1991

[51] Int. Cl.[5] ..... A01H 5/00

[52] U.S. Cl. ..... Plt./53.2

[58] Field of Search ..... Plt./53.2

[56] References Cited

U.S. PATENT DOCUMENTS

P.P. 7,732 12/1991 Orton ..... Plt. 53.2

*Primary Examiner*—James R. Feyrer

*Attorney, Agent, or Firm*—Frank B. Robb

[57] ABSTRACT

The plant hereof is notable for its dark red floral bracts and rather small compact form of tree characterized by branching of a densely profuse form being more dense than other clones of *C. florida*.

1 Drawing Sheet

BACKGROUND OF THE INVENTION

Our new cultivar is the product of a long standing detailed program of hybridizing and selection of dogwood in this instance from native Eastern or *Cornus florida* seedlings which are carefully controlled, records carefully retained and characteristics analyzed for their differences and outstanding value as potential commercial varieties or cultivars.

As will be understood from the following the program has resulted in many outstanding crosses which ultimately result in particularly attractive vegetative and floral parts, which appear on trees which are very floriferous and regular bearers.

We have selected the particular seedling hereof from certain progeny grown in a cultivated area and as a result have in turn caused the same to be asexually reproduced by stem cuttings. They may also be so reproduced by budding and grafting.

The reproduction and actual growth and selection of the new cultivar took place in the vicinity of New Brunswick, N.J. and has been found to be distinctive as to its winter-hardiness in that area, Plant Hardiness Zone 6.

As will be understood from the detailed description of the invention which appears hereinafter, the new cultivar is in fact outstanding and readily identified as being such thus providing for a new variety which is identified botanically for the purposes hereof as *Cornus florida* L. var. rubra West and will be known commercially as 'D-376-15' the identifier which it was assigned when selected, and has for local identification, the synonym 'Rutnam'.

With the foregoing in mind the description which follows will be understood as clearly defining the new cultivar as having the desirable characteristics which are the result of such a program as been here heretofore suggested.

In order to completely disclose the new plant hereof, there is shown herewith in FIG. 1 a typical tree of the new variety to illustrate the density and relative wide spread nature as well as the short height thereof.

FIG. 2 discloses a flower head at the time of flowering and indicates the color and shape of the floral bracts.

Where color is referred to, the color chart of The Royal Horticultural Society is availed of to designate the same, recognizing that the color is as nearly accurate as it is possible to provide by photographic processes.

DETAILED DESCRIPTION OF THE INVENTION

Figure 1:
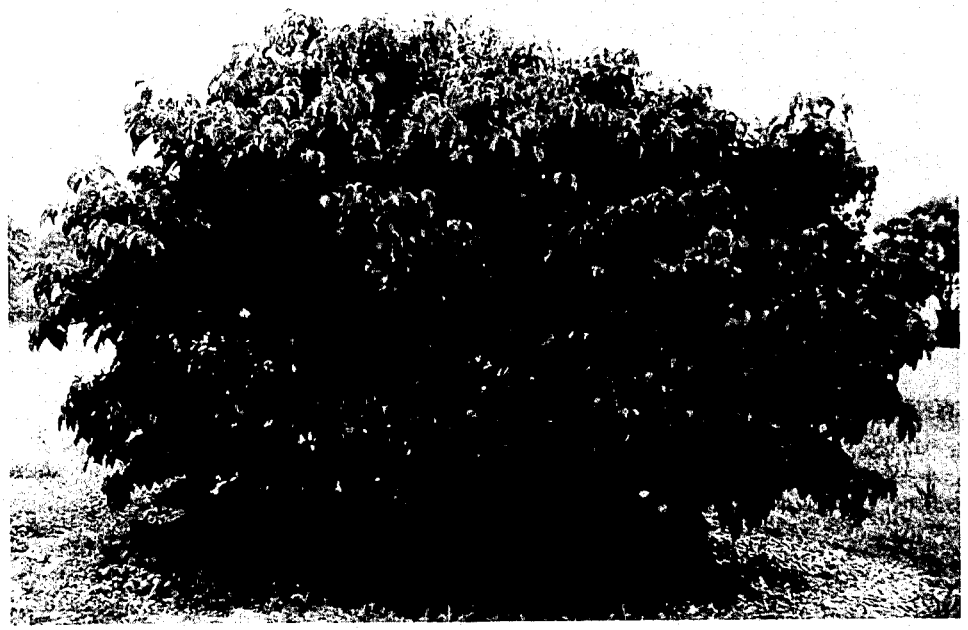
Figure 2:
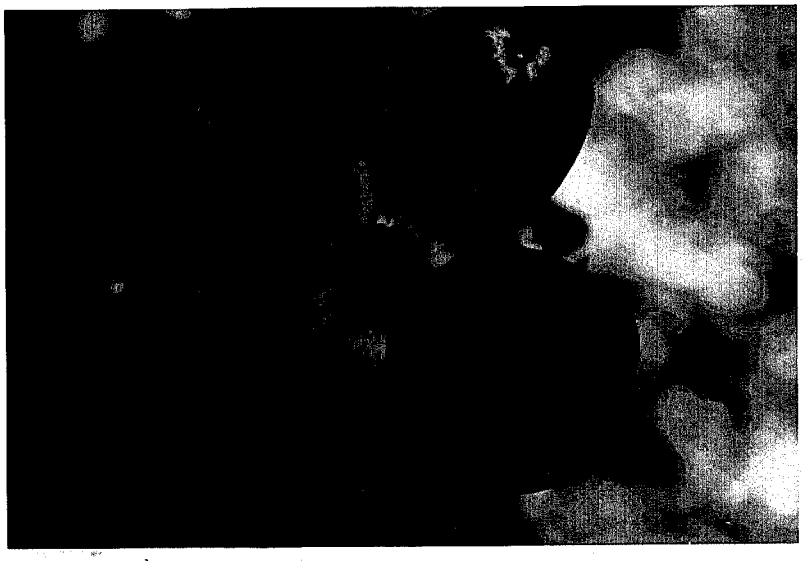

Origin: A seedling selection from the progeny of a controlled cross of two select seedlings each of which originated from a cross of a plant of *C. florida* var. rubra × a plant of *C. florida* 'Pygmy', the rubra plants in the two initial crosses being unrelated in origin.

Where reproduction took place: Reproduction took place in the vicinity of New Brunswick, N.J.

Classification:

*Botanic name.*—*Cornus florida* L. var. rubra West.

*Commercial name.*—'D-376-15'.

Tree: Small and rounded in shape. Smaller and more compact than other rubra clones tested, such as 'Cherokee Chief', 'Prosser Red', 'Sweetwater', 'Spring Song', and 'Welch's Jr. Miss', however it is not a dwarf plant. Vegetative and floral parts have been fully winter-hardy at New Brunswick, N.J., Plant Hardiness Zone 6. Very floriferous. Regular bearer.

Trunk: Smooth as a young plant but bark becomes shaggy with age as is typical for plants of *C. florida*. Color of trunk or bark is 197C (Greyed-Green Group on the R.H.S. Colour Chart of The Royal Horticultural Society, London.

Branches: Medium to stocky, with an unusually high number of side branches which causes the tree to be more compact and heavily branched than other rubra clones, such as 'Prosser Red', currently in the trade. Smooth. 197C (Greyed-Green Group). 2.8 meters in height and 4.03 meters in width as a typical tree.

Leaves: Elliptic, with base broadly cuneate (sometimes mildly oblique) and tip abruptly acuminate.

*Length.*—8.8 to 16.5 cms. long.

*Width at widest point*—5.0 to 9.7 cms.

*Petiole length.*—0.9 to 1.9 cms.

*Color.*—Upper surface is 137A (Green Group). Lower surface is 138B (Green Group).

Flower Buds: Medium to large, nearly globose with rather flattened base — Width ranges from 5.5 to 8.0 mm. Height ranges from 5.5 to 8.5 mm. True flowers are tiny and relatively inconspicuous (each with four minute petals), are borne in dense heads, and are enclosed over winter by four involucral bracts that subtend the true flowers.

Involucral, or floral, bracts:

*Color.*—When fully expanded: Upper surface 184C (Greyed-Purple Group); about the same as that of the floral bracts of 'Prosser Red', but darker in color than the floral bracts of 'Sweetwater' or 'Spring Song', both of which exhibit more white at the base of the floral bracts.

*Size and shape.*—When the floral bracts are fully expanded, the diameter of the involucre from tip to tip of the opposing inner bracts is about 95.6 mm.; the diameter of the involcure as measured from tip to tip of the opposing outer bracts is approximately 84.3 mm. The average length of the inner and outer bracts is about 46 mm. and 41 mm., respectively. The width of the inner and outer bracts at their widest point is about 37.1 and 40.7, respectively. Length and width of the floral bracts can vary considerably from year to year, but the inner bracts most likely will be both longer and more narrow than the outer bracts in any given year. In general, the outer bracts are nearly equal in length and width and are broadly tapered at the base, whereas the inner bracts are longer than wide and are more narrowly tapered at the base. In general, the floral bracts would be considered obovate with an emarginate tip.

*Peduncle length.*—Each flower head is borne on a peduncle, the average length of which is about 34 mm. at the time of flowering and/of floral display. The absolute peduncle length will vary slightly from year to year.

*Flowering and floral display.*—The period of floral display (floral bracts) is typical of that for most plants of *C. florida;* i.e., occurring in late April and early May in the vicinity of New Brunswick, N.J., and extending for a period of 10–15 days, depending on weather conditions. Anthesis of the tiny, relatively inconspicuous, true flowers commences two to four days after the onset of the ornamental display of the large floral bracts and continues for about seven to ten days, depending on weather conditions. The average number of true flowers per flower head in our new intraspecific hybrid is about 19.7, whereas that of 'Prosser Red' is stated to have floral bracts of a similar color, is about 26.2; characteristic is quite consistent from year to year. 'D-376-15' is a more compact plant than is 'Prosser Red'.

*Fruit.*—The fruit are avoid, approximately 11 to 14 mm. long and bright red, 45A and/or 46B, (Red Group) as is rather typical of the fruit of most plants of *C. florida.*

Resistance to:

*Insects.*—The relative resistance, or susceptibility, of plants of 'D-376-15' to the various insect pests known to attack plants of *C. florida* is expected to be typical of that of plants of most cultivars of *C. florida.*

*Diseases.*—The relative resistance, or susceptibility, of plants of 'D-376-15' to the various disease organisms known to attack plants of *C. florida* is assumed to be typical of that exhibited by most plants of *C. florida* but little information is available at this time.

We claim:

1. A new and distinct cultivar of dogwood tree, substantially as herein shown and described, characterized particularly as to novelty by the unique combination of its dark red, floral bracts and the rather small, compact rounded form of tree which results from the characteristic of branching more densely and profusely than other plants of *C. florida* var. rubra.

* * * * *